US010366375B2

(12) United States Patent
Hoover et al.

(10) Patent No.: US 10,366,375 B2
(45) Date of Patent: Jul. 30, 2019

(54) AUTOMATED TRANSACTION MACHINE WITH DUAL CUSTOMER INTERFACE DISPLAYS

(71) Applicant: Diebold Self-Service Systems, Division of Diebold, Incorporated, North Canton, OH (US)

(72) Inventors: Timothy Hoover, Canton, OH (US); Donald Nelson, Jr., Akron, OH (US); Todd Christian, Dalton, OH (US); Neil Gromley, Kensington, OH (US)

(73) Assignee: Diebold Nixdorf Incorporated, North Canton, OH (US)

( * ) Notice: Subject to any disclaimer, the term of this patent is extended or adjusted under 35 U.S.C. 154(b) by 645 days.

(21) Appl. No.: 14/965,235

(22) Filed: Dec. 10, 2015

(65) Prior Publication Data

US 2016/0171461 A1 Jun. 16, 2016
US 2017/0091729 A9 Mar. 30, 2017

Related U.S. Application Data

(60) Provisional application No. 62/090,094, filed on Dec. 10, 2014.

(51) Int. Cl.
*C12Q 1/689* (2018.01)
*G06Q 20/10* (2012.01)
*G06F 3/0488* (2013.01)

(52) U.S. Cl.
CPC ........ *G06Q 20/1085* (2013.01); *C12Q 1/689* (2013.01); *G06F 3/0488* (2013.01)

(58) Field of Classification Search
None
See application file for complete search history.

(56) References Cited

U.S. PATENT DOCUMENTS

| 9,235,967 | B1 * | 1/2016 | Magee | G07F 19/201 |
| 2006/0038004 | A1 * | 2/2006 | Rielly | G06Q 20/1085 |
| | | | | 235/379 |
| 2014/0118466 | A1 * | 5/2014 | Chang | G06Q 40/02 |
| | | | | 348/14.04 |

OTHER PUBLICATIONS

Nautilus Hyosung Press Release regarding release of the MX8800—dated Aug. 25, 2014.

* cited by examiner

*Primary Examiner* — Kristy A Haupt
(74) *Attorney, Agent, or Firm* — Black. McCuskey, Souers & Arbaugh, LPA

(57) ABSTRACT

In an example embodiment, described herein is an automated transaction machines with dual customer interface displays of different sizes and different orientations, configured for selective use by a customer by selection of desired display option for a financial transaction.

15 Claims, 5 Drawing Sheets

AUTOMATED TRANSACTION MACHINE WITH DUAL CUSTOMER INTERFACE DISPLAYS

CROSS REFERENCE TO RELATED APPLICATIONS

This application claims the benefit under 35 U.S.C. § 119 of U.S. Provisional Application No. 62/090,094 filed Dec. 10, 2014, the entire application is hereby incorporate by reference herein.

TECHNICAL FIELD

The present disclosure relates generally to a user interface for an automated transaction machine ("ATM").

BACKGROUND

Automated transactions machines and automated banking machines are designed and configured to carry out financial transactions such as dispensing cash, accepting deposits such as cash and checks and other notes or documents or envelopes, and may be capable of performing other financial transactions such as funds transfers between accounts by connection to one or more financial networks. As referred to herein, the term automated transaction machine (ATM) includes automated banking machines and any machine or device, or combination of hardware and software which perform financial transactions or transfers of value.

BRIEF DESCRIPTION OF THE DRAWINGS

The accompanying drawings incorporated herein and forming a part of the specification illustrate the example embodiments.

OVERVIEW OF EXAMPLE EMBODIMENTS

Figure 1:
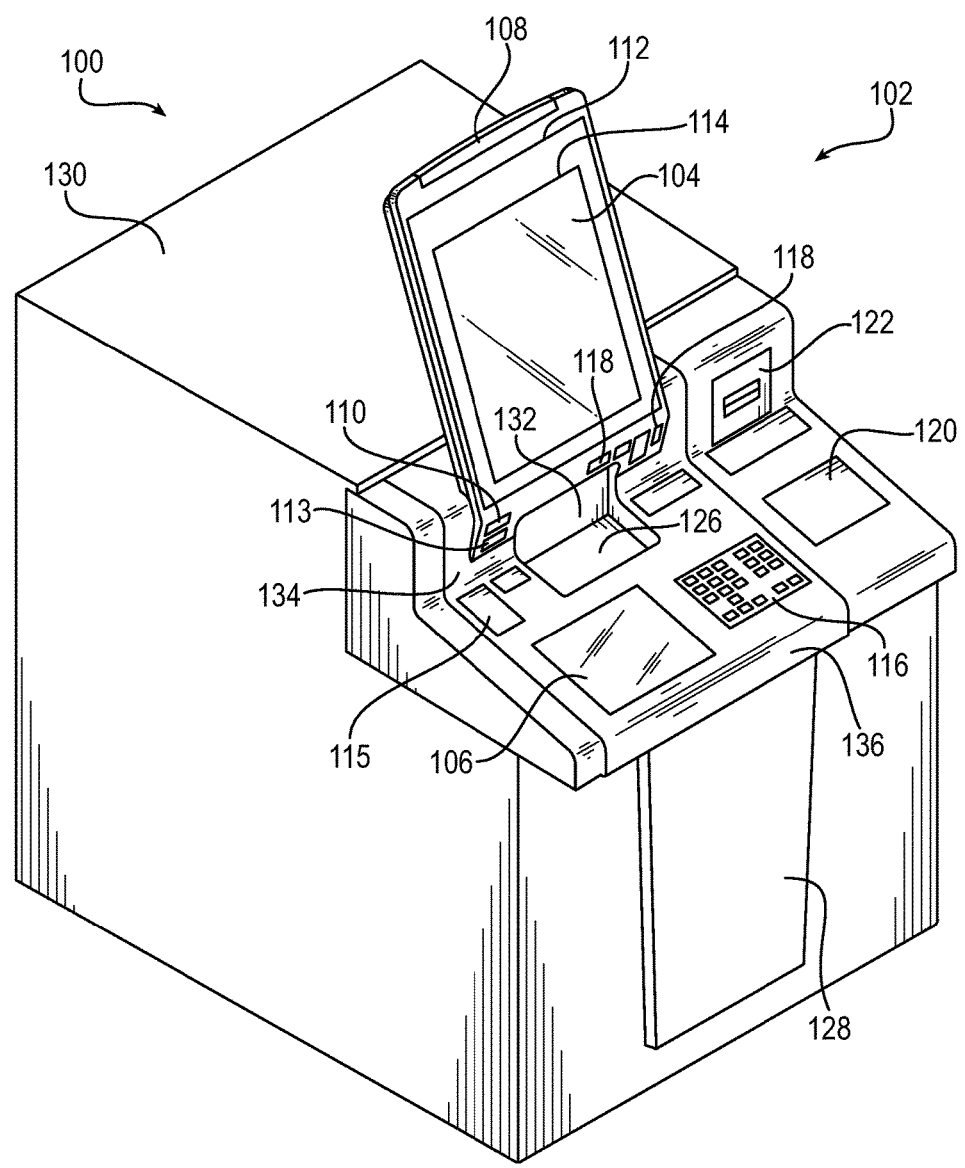
FIG. 1 is a perspective view of a representative embodiment of an In Lobby Teller (ILT) ATM which has a customer interface with first and second displays.

The following presents a simplified overview of the example embodiments in order to provide a basic understanding of some aspects of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented later.

In accordance with an example embodiment, a user interface with dual displays. The first display is oriented in a first direction. The second display is smaller than the first size and oriented in a (different) second direction. Display logic coupled with the first and second displays is operable to control the operation of the first and second displays. The display logic allows a user to select a display mode for financial transaction, such as for example, transaction information displayed on the first display while the second display is blank, display transaction on the second display while the first display is blank, toggling between employing the first display and second display for a transaction, simultaneously displaying transaction data on both the first display and the second display, concurrently displaying transaction data on both the first display and the second display, or displaying public information on the first display while displaying private information on the second display.

DESCRIPTION OF EXAMPLE EMBODIMENTS

This description provides examples not intended to limit the scope of the appended claims. The figures generally indicate the features of the examples, where it is understood and appreciated that like reference numerals are used to refer to like elements. Reference in the specification to "one embodiment" or "an embodiment" or "an example embodiment" means that a particular feature, structure, or characteristic described is included in at least one embodiment described herein and does not imply that the feature, structure, or characteristic is present in all embodiments described herein.

ATMs in the various embodiments disclosed herein have a customer interface which includes first and second displays. A first display is of a first size and in a first position and first orientation. A second display is of a second size and in a second position and second orientation. In a first example embodiment, the first display is located generally vertically above the second display, and the first size of the first display is larger than the second size of the second display. In a second example embodiment, the first orientation of the first display is generally vertical and the second orientation of the second display is generally horizontal, as will be further described herein. In other embodiments, the first display is located generally vertically above the second display, and the first size of the first display is larger than the second size of the second display, and both the first display and second display are generally vertically oriented. In particular embodiments, the second display may be equal or larger than the first display. As used herein, generally vertical is within forty-five degrees of the vertical axis while generally horizontal is within forty-five degrees of an axis that is orthogonal to the vertical axis.

A customer interface in an example embodiment described herein comprises a first display in a first or uppermost position and first orientation such as generally vertical or vertical in a rearwardly slanted or tilted or easel orientation, the first display in a in either a landscape or portrait orientation and able to be mounted or adjusted to any such orientation, the first display being of a first size and may be a SXGA ("Super-eXtended Graphics Array") type color display, touch screen enabled, sunlight viewable and with privacy filter, and a second display in a second location generally at a lower height than the first display and in a second orientation different than the first orientation of the first display and in an example embodiment in a generally horizontal orientation or slightly inclined plane inclined toward a front of the ATM customer interface, the second display being of a second display size that is less than a display size of the first display, the second display may be a touch screen enabled display and optionally configured as a virtual PIN pad; a scanner with a scanning window and/or signature window that is co-located or in place of the display screen of the second display. Optionally, the user interface may further include, but is not limited to, one or any combination of the following components, modules and devices: a service teller call beacon; one or more consumer facing cameras, one or more microphones, one or more speakers, a contactless card reader such as a near-field communication (NFC) device; an encrypting PIN (Personal Identification Number) pad, a headphone jack, a receipt printer such as for example a 80 mm enhanced graphical printer; a card reader such as for example an EMV (Europay, MasterCard, and Visa) card reader which may be configured for short-edge or long-edge card insertion and reading, MCR (Magnetic Ink Character Recognition) or a DIP card reader, a 2D barcode or QR (Quick Response) code scanner or document scanner, a mixed deposit module opening for receipt of currency, documents, notes, tickets or any other medium of transaction, a biometric reading device such as a fingerprint reader or retinal detector; and a fascia assembly as depicted herein. In particular embodiments, the first display may comprise a scanning window and/or a signature window.

The differing location, size and orientation between the first display and second display can be advantageous for improved ergonomics and operating ease. The dual displays of the customer interfaces of the ATMs of the present disclosure allow for easier access and operation by customers regardless of customer height and position (standing or sitting, such as for example a person confined to a wheelchair). The different orientation of the first and second displays allows a customer to select a display of their preference for conducting a transaction. The choice including size of the display and the information presented thereon, and the orientation of the display between generally "head-up" and "head-down". The ATM can be configured to have the first display and second display operate simultaneously, e.g. displaying the same information at the same time, or to display different information or graphics, such as for example an image of a teller or teller avatar or advertisement or other information on the first display, and transaction information or documents on the second display. Alternatively, the ATM may be configured to allow for customer selection of the first or second display for conducting a transaction, which selection may deactivate the display not chosen. This control may be incorporated into the customer interface or as a control that is operated by one of the touch screen displays. For example, a control or instruction as simple as "select display" or "select screen" at the start of the transaction, by touching the selected screen, will then deactivate the other non-selected display. Alternatively, the ATM may be configured to enable a customer to switch or toggle between the first or second displays during a transaction. This is a desirable function for using the larger first display in an attract or standby or transaction initiation mode, and then switching to the smaller second display before the private transaction details are displayed. Another operational configuration is to use the first display for customer attraction or advertising and transaction initiation, and the second display exclusively for display of private transaction details. Another ATM function which can be included in the control software is to use the larger first display for display of ATM operation instructions, prompts, responses or other generic or non-private information pertaining to a transaction, while all personal or private information is displayed on the smaller second display.

In an example embodiment, the generally horizontal orientation of the second display is significantly more concealed to the ATM user, e.g., much more difficult to view by people in line behind the user or at the side of the ATM. The display screen of the second display is located in a counter structure of the ATM which projects from front fascia generally horizontally and at a slight downward angle. In an example embodiment, the counter surface height is ergonomically suited for users in a wheelchair or in similar mobile conveyances, and from which vantage the user may prefer either the first display or second display, and control the selection thereof as explained. The generally horizontal orientation of the second display can be advantageous when the second display is configured as a scanner for placement of documents thereon. Any of the various embodiments of the dual display ATM customer interfaces can also be implemented in outdoor, through-the-wall or drive-up configurations, as depicted herein.

ATMs of the present disclosure may include or otherwise be in part or any of the following configurations, including transaction function devices may include a document dispensing mechanism, including a dispenser which operates to cause sheets such as currency bills or other documents of value stored within the machine to be delivered from the machine to a machine user. Such mechanisms are referred to herein as a cash dispenser. Examples of such cash dispensers are shown in U.S. Pat. Nos. 7,121,461; 7,131,576; 7,140,537; 7,140,607; 7,144,006; and 7,000,832 the disclosures of which are incorporated herein by reference.

The ATMs of the present disclosure may further include a depository operative to accept deposits such as cash or other instruments such as checks from customers. It should be understood that in other embodiments other types of depositories which accept various types of items representative of value may be used. Examples of depository devices are shown in U.S. Pat. Nos. 7,156,295; 7,137,551; 7,150,394; and 7,021,529 the disclosures of which are incorporated hereby by reference. Exemplary ATMs may also include a note acceptor of the types described in the incorporated disclosures. The exemplary embodiment may include a receipt printer operative to print customer receipts related to the transaction. The exemplary embodiment may include other transaction function devices, such as a coin dispenser, coin acceptor, currency stacker, ticket accepting devices, stamp accepting devices, card dispensing devices, money order dispensing devices, and other types of devices which are operative to carry out transaction functions. Some of these devices may be located in the upper or lower housing areas as depicted in the accompanying Figures, the depicted embodiments being representative and illustrative of various embodiments of the ATMs of the disclosure and related inventions.

FIG. 1 is a perspective view of a representative embodiment of an ILT ATM 100 which has a customer interface 102 with first and second displays 104, 106 respectively. The operation of the first and second displays 104, 106 will be described in more detail herein infra (see e.g., FIG. 4).

In the illustrated example, the first display 104 is at a first height, taller than the second display 106 and oriented in a substantially vertical direction as depicted. In an example embodiment, the first display 104 is a 19 inch SXGA display. In particular embodiments, the first display 104 comprises a touch screen or an encrypting touch screen interface. In yet other example embodiments, the first display 104 comprises a document scanner. In still yet other example embodiments, the first display 104 comprises a signature scanner. As those skilled in the art can readily appreciate, the first display 104 may suitably comprise any combination of a touch screen, document scanner, or signature scanner. In an example embodiment, the first display 104 may suitably comprise a virtual PIN pad, and in particular embodiments, the virtual PIN pad is an encrypting PIN pad.

In the illustrated example, the second display 106 is oriented in a different (e.g., substantially horizontal) direction and is smaller than the first display. In an example embodiment, the second display 106 is a 10.4 inch display. In an example embodiment, the second display 106 can be a touch screen enabled display and optionally configured as a virtual PIN pad or with a scanning window or signature capture device co-located or in place of the display screen of the second display 106.

The differing location, size and orientation between the first display 104 and the second display 106 can ergonomically beneficial and provide operating ease. The dual displays 104, 106 of the customer interface 102 of the ATM 100 allow for easier access and operation by customers regardless of customer's height and/or position (standing or sitting, such as for example a person confined to a wheelchair or similar device). The different orientation of the first and second displays 104, 106 allows a customer to select a display of their preference for conducting a transaction. The choice including size of the display and the information presented thereon, and the orientation of the display between generally "head-up" and "head-down". The ATM 100 can be configured to have the first display 104 and second display 106 operate simultaneously, e.g. displaying the same information at the same time (or concurrently), or to display different information or graphics, such as for example an image of a teller or teller avatar, advertisement, or other information on the first display 104, while displaying transaction information or documents on the second display 106. Alternatively, the ATM 100 may be configured to allow for customer selection of the first 104 or second 106 display for conducting a transaction, which selection may deactivate the display not chosen. This control may be incorporated into the customer interface or as a control that is operated by one of the touch screen displays. For example, a control or instruction as simple as "select display" or "select screen" at the start of the transaction, by touching the selected screen, will then deactivate the other non-selected display. Alternatively, the ATM 100 may be operable to enable a customer to switch or toggle between the first 104 or second 106 displays during a transaction. This is a desirable function for using the larger first display 104 in an attract customer or standby or transaction initiation mode, and then switching to the smaller second display 106 before the private transaction details are displayed. Another operational configuration option is to use the first display 104 for customer attraction or advertising and transaction initiation, and the second display 106 exclusively for the display of private transaction details. Another ATM function which can be included in the control software (or logic as will be described in more detail herein infra) is to use the larger first display 104 for the display of ATM operation instructions, prompts, responses or other generic or non-private information pertaining to a transaction, while personal or private information is displayed on the smaller second display 106 which is also oriented to better conceal the information from persons behind the customer. Although the description herein describes the first display 104 as larger than the second display 106, those skilled in the art can appreciate that in particular embodiments the second display 106 may be equal or larger than the first display 104.

In an example embodiment, the generally horizontal orientation of the second display 106 can provide more concealment to the ATM user, (e.g., it is more difficult to view by people in line behind the user or standing at the side of the ATM 100). The display screen of the second display 106 is located in a counter structure 136 of the ATM 100 which projects from front fascia 134 in a generally horizontally direction and at a slight downward angle. In an example embodiment, the counter surface height is ergonomically suited for users in a wheelchair or in similar mobile conveyances, and from which vantage the user may prefer either the first display 104 or second display 106, and control the selection thereof as explained herein. The generally horizontal orientation of the second display 106 can be advantageous when the second display 106 is configured as a scanner for placement of documents thereon.

In the illustrated example, the ATM 100 further comprises a teller help/call button light 108. A customer can request teller assistance by pushing the teller call button 110. The teller help/call button light can change colors and/or flash upon activation of the teller call button 110. For example, the teller help/call button light 108 may be green in a normal operating mode, but turn red and/or flash in response to c customer pressing the teller call button 110.

Optionally, as depicted in the illustrated example, the ATM 100 may further comprise one or more of a consumer face camera 112, a 2-way video camera 114, a Near Field Communication (NFC) interface 115, a keypad 116, a headphone jack 118, receipt printer 120, card reader 122, 2 dimensional, e.g., QR, barcode reader 124, cash recycler 126, chest 128, countertop 130, and cash slot camera 132. As those skilled in the car can readily appreciate, other embodiments may include any combination of the aforementioned devices. For example, in embodiments where one or both of the first display 104 and second display 106 are touch screens, there may not be a keypad. Similarly, some embodiments, may have only a card reader while other embodiments may only have a NFC interface for identifying a customer. Other embodiments may have a cash dispenser instead of a cash recycler. Still other embodiments may have a deposit input for accepting cash, checks, and/or other documents.

Figure 2:
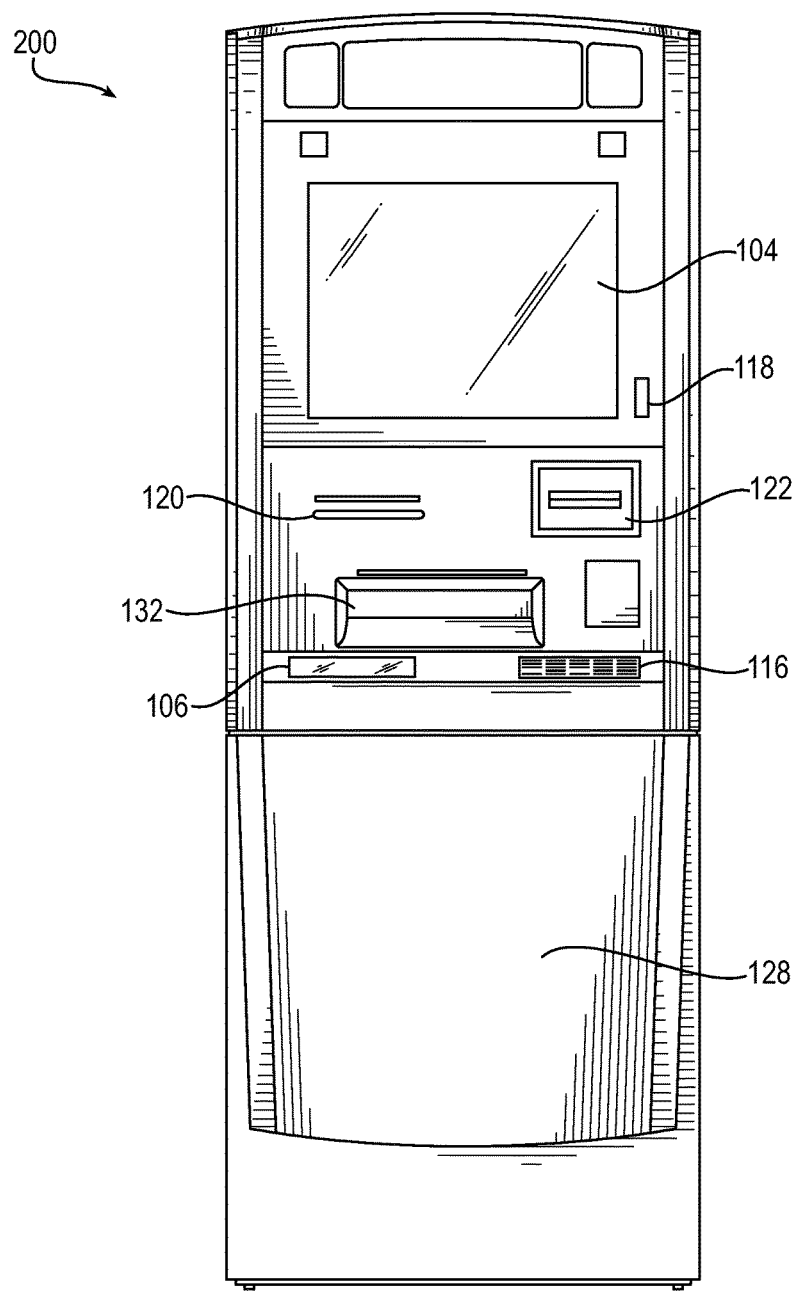
FIG. 2 illustrates an example of a standalone ATM which has a customer interface with first and second displays.
Figure 3:
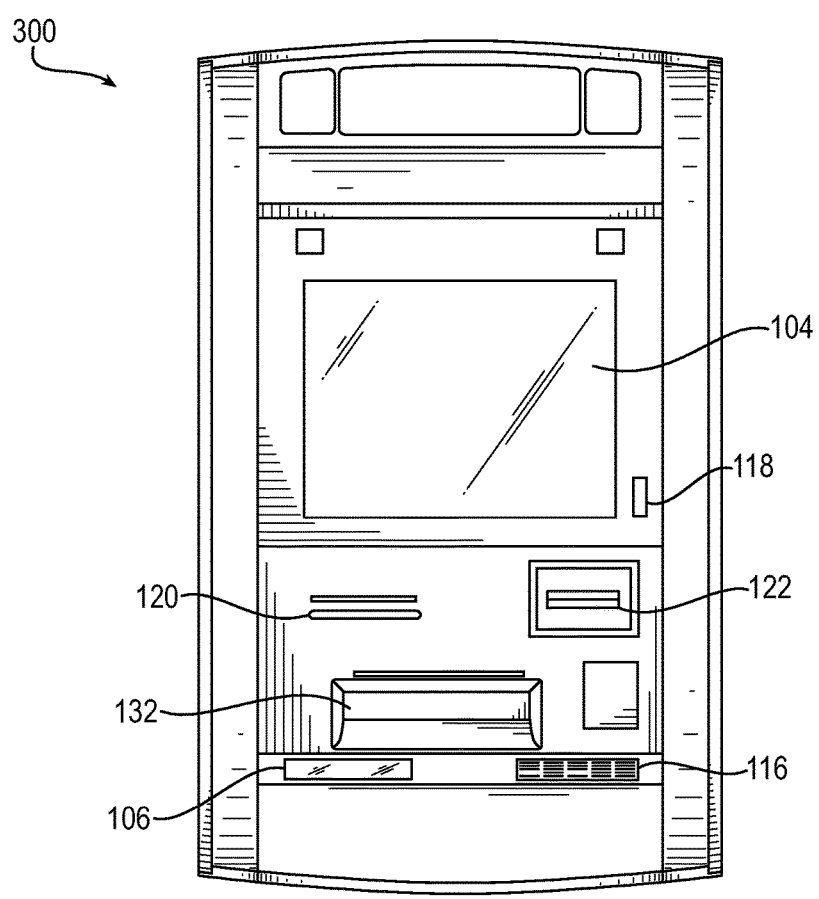
FIG. 3 illustrates an example of an ATM in a through-the-wall configuration which has a customer interface with first and second displays.

Any of the various embodiments of the dual display ATM 100 customer interfaces can also be implemented in outdoor, through-the-wall or drive-up configurations, as depicted herein. For example, FIG. 2 illustrates a illustrates an example of a standalone ATM 200 which has a customer interface with first and second displays 104, 106. FIG. 3 illustrates an example of an ATM 300 in a through-the-wall configuration which has a customer interface with first and second displays 104, 106. In an example embodiment, the first display 104 of ATM 200 and/or 300 is fifteen inches while the second display 106 is seven inches. In another example embodiment, the first display 104 of ATM 200 and/or 300 is nineteen inches while the second display 106 is seven inches. As those skilled in the art can readily appreciate, ATM 200 or 300 may also include any of the devices mentioned in the description of FIG. 1 supra.

Figure 4:
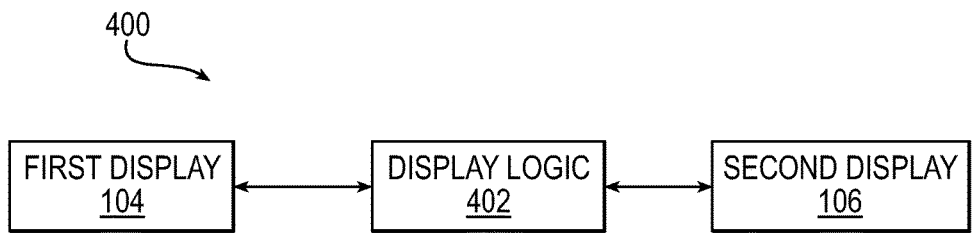
FIG. 4 is a logical block diagram illustrating an example of a dual display interface suitable for use with an ATM.

FIG. 4 is a logical block diagram illustrating an example of a dual display interface 400 suitable for use with an ATM. The dual display interface 400 comprises a first display 104 and a second display coupled with display logic 402. "Logic", as used herein, includes but is not limited to hardware, firmware, software and/or combinations of each to perform a function(s) or an action(s), and/or to cause a function or action from another component. For example, based on a desired application or need, logic may include a software controlled microprocessor, discrete logic such as an application specific integrated circuit (ASIC), a programmable/programmed logic device, memory device containing instructions, or the like, or combinational logic embodied in hardware. Logic may also be fully embodied as software that performs the desired functionality when executed by a processor.

In an example embodiment, the first display 104 is a first size (e.g., 15 or 19 inches) and has a first orientation, such as for example, a generally vertical orientation as depicted in FIGS. 1-3. The second display 106 is a second size (e.g., 7 inches) that is less than the first size and a second orientation that is different from the first orientation (e.g., generally horizontal as depicted in FIGS. 1-3).

In an example embodiment, the display logic 402 is operable to allow a user to select a mode of operation for the first display 104 and the second display 106. In an example embodiment, the mode of operation is selected from a group consisting of displaying transaction information on the first display 104 while blanking the second display 106, and displaying transaction information on the second display 106 while banking the first display 104. In another example embodiment, the mode of operation is selected from a group consisting of displaying transaction information on the first display 104 while blanking the second display 106, displaying transaction information on the second display 106 while banking the first display 104 and toggling between displaying transaction data on the first display 104 and displaying transaction on the second display 106. In still yet another example embodiment, the mode of operation is selected from a group consisting of displaying transaction information on the first display 104 while blanking the second display 106, displaying transaction information on the second display 106 while banking the first display 104, and one of a group consisting of concurrently and simultaneously displaying information on both the first display 104 and the second display 106. In particular embodiments the display logic 402 is operable to save a user selection as a default mode for the user.

In an example embodiment, the display logic 402 is operable to display public data on the first display 104 and private data on the second display 106. Examples of public data include, but are not limited to, customer attention, advertisement, transaction initiation data. Examples of private data include but are not limited to, private transaction data, such as for example account balance, account number, or transaction amount. The display logic 402 can be operable to allow a user to select a mode of operation for the first display 104 and the second display 106. Example modes of operation include, but are not limited to, displaying transaction information on the first screen while blanking the second display, displaying transaction information on the second display while banking the first display, toggling between displaying transaction data on the first display and displaying transaction on the second display, and simultaneously displaying information on both the first display and the second display.

Figure 5:
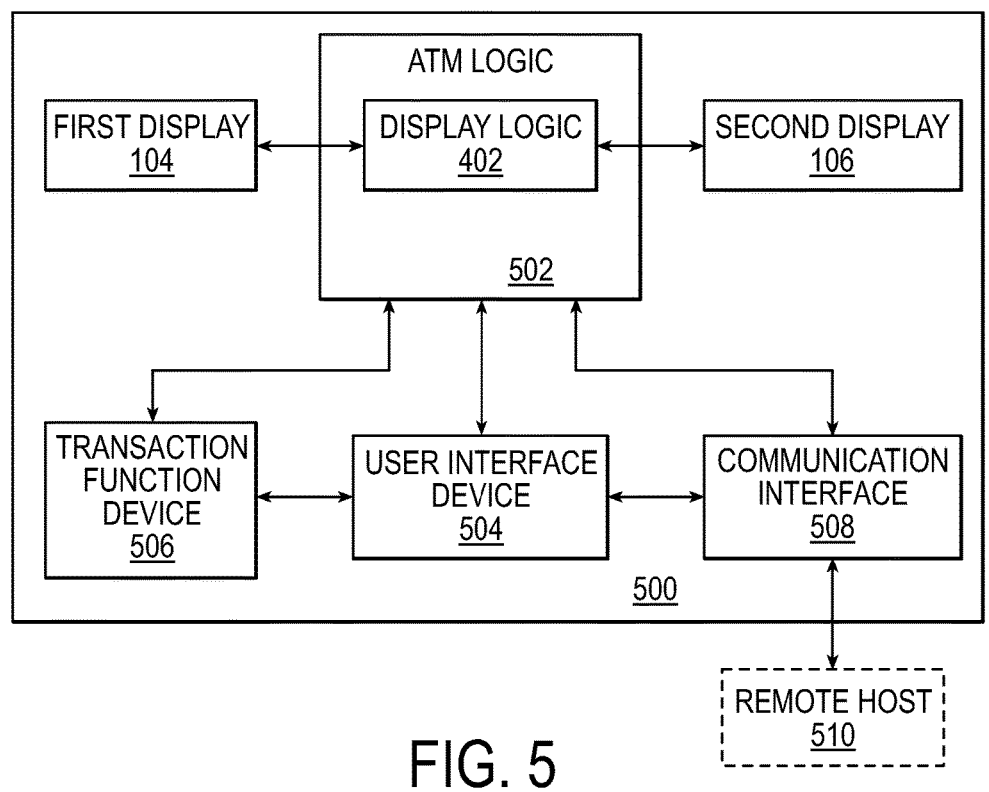
FIG. 5 is a logical block diagram illustrating an example of an ATM with first and second displays.

FIG. 5 is a logical block diagram illustrating an example of an ATM 500 with first and second displays 104, 106. The display logic 402 may operate as described in FIG. 4 supra. The ATM 500 further comprises ATM logic 502 which is operable to perform financial transactions and can provide data to display on the first display 104 and the second display 106. For example, the ATM logic 502 may be employed to implement the functionality described herein for ATMs 100, 200, 300 described in FIGS. 1-3 respectively.

In an example embodiment, the ATM logic 502 is coupled with an additional user interface device 504. The additional user interface device 504 may be any one or more of (but not limited to) a card reader (which may be configured for long-edge or short-edge card insertion, such as a DIP reader), a NFC interface which can allow a user to communicate with the ATM logic 502 using a portable wireless device such as a mobile phone, a keypad, an encrypting PIN pad, a headphone jack, one or more speakers, a receipt printer, an EMV card reader, a service teller call light, a service teller call button, a barcode (e.g., 2D or QR) reader, or a biometric reading device.

In an example embodiment, the ATM logic 502 is coupled with at least one transaction function device 506. Examples of a transaction function device include, but are not limited to, a cash dispenser, a cash recycler, a mixed deposit module (for example for receiving cash and documents such as checks), a cash deposit module, a document deposit module and a document output device (e.g., can provide printed checks, money orders, or other documents).

In an example embodiment, the ATM logic 502 is coupled with a communication interface 508 that allows the ATM logic 502 to communicate with a remote host (or a plurality of remote hosts) 510. For example, the ATM logic may communicate with a remote host 510 to authenticate a user. The user may employ any user device, such as the first display 104, second display 106, or additional user interface device 504 (or any combination of use interface devices) to provide data representative of the user, and in particular embodiments, data representative of a PIN. The ATM logic 502 communicates with the remote host 510 to authenticate the data representative of the user and data representative of a PIN. Upon authenticating a user, the ATM logic 502 may obtain from the remote host 510, data representative of accounts associated with the user. The ATM logic 502 receives data representative of a transaction from any one or more user interface devices such as first display 104, second display 106, or additional user interface device 504. For some transactions, the ATM logic can obtain authorization for the transaction by communicating with remote host 510. For example, the ATM logic 502 may obtain authorization for a cash withdrawal transaction, and responsive to receiving authorization for the transaction employ a transaction function device 506 to provide cash to the user. As those skilled in the art can readily appreciate, different remote hosts may be employed for authenticating a user and authorizing a transaction.

Figure 6:
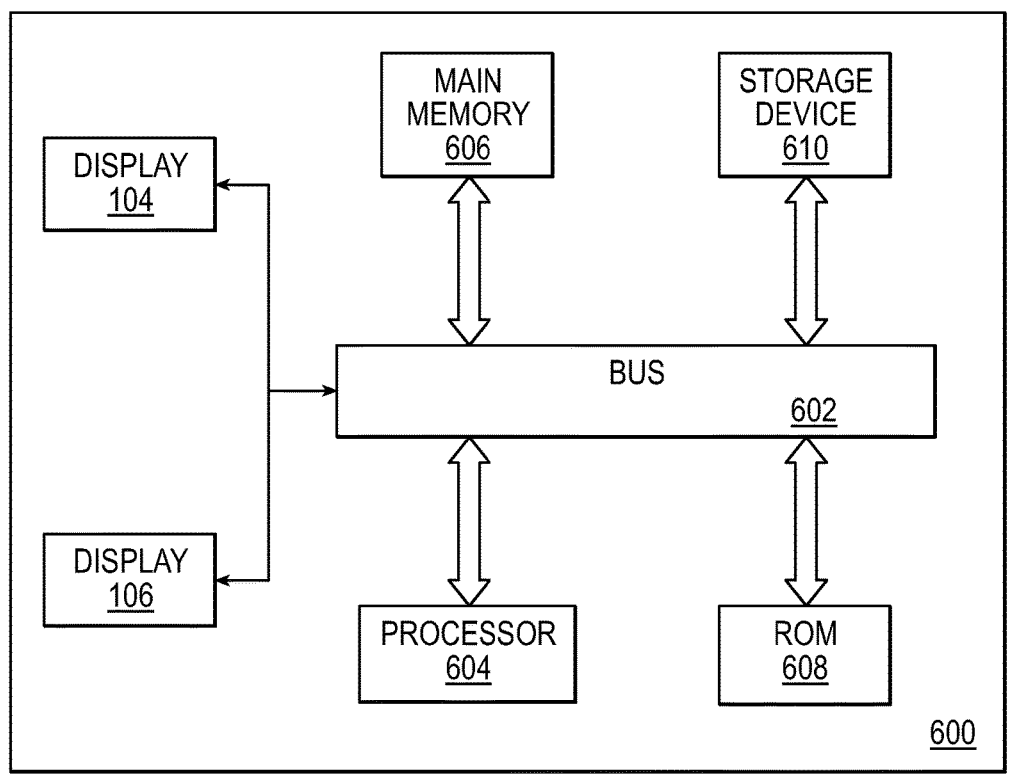
FIG. 6 is a block diagram of a computer system upon which an example embodiment can be implemented.

FIG. 6 is a block diagram of a computer system 600 upon which an example embodiment can be implemented. The computer system 600 can be employed to implement the dual screen interface described in FIGS. 1-4, and for implementing display logic 402 described in FIGS. 4 and 5 and/or the ATM logic 502 described in FIG. 5.

Computer system 600 includes a bus 602 or other communication mechanism for communicating information and a processor 604 coupled with bus 602 for processing information. Computer system 600 also includes a main memory 606, such as random access memory (RAM) or other dynamic storage device coupled to bus 602 for storing information and instructions to be executed by processor 604. Main memory 606 also may be used for storing a temporary variable or other intermediate information during execution of instructions to be executed by processor 604. Computer system 600 further includes a read only memory (ROM) 608 or other static storage device coupled to bus 602 for storing static information and instructions for processor 604. A storage device 610, such as a magnetic disk or optical disk, is provided and coupled to bus 602 for storing information and instructions.

In an example embodiment, computer system 600 is coupled via bus 602 to first 104 and second 106 displays. An aspect of the example embodiment is related to the use of computer system 600 for implementing an automated transaction machine with a dual customer interface displays. According to an example embodiment, an automated transaction machine with a dual customer interface displays is provided by computer system 600 in response to processor 604 executing one or more sequences of one or more instructions contained in main memory 606. Such instructions may be read into main memory 606 from another computer-readable medium, such as storage device 610. Execution of the sequence of instructions contained in main memory 606 causes processor 604 to perform the process steps described herein. One or more processors in a multi-processing arrangement may also be employed to execute the sequences of instructions contained in main memory 606. In alternative embodiments, hard-wired circuitry may be used in place of or in combination with software instructions to implement an example embodiment. Thus, embodiments described herein are not limited to any specific combination of hardware circuitry and software.

The term "computer-readable medium" as used herein refers to any medium that participates in providing instructions to processor 604 for execution. Such a medium may take many forms, including but not limited to non-volatile media. Non-volatile media include for example optical or magnetic disks, such as storage device 610. Common forms of computer-readable media include for example floppy disk, a flexible disk, hard disk, magnetic cards, paper tape, any other physical medium with patterns of holes, a RAM, a PROM, an EPROM, a FLASHPROM, CD, DVD or any other memory chip or cartridge, or any other medium from which a computer can read.

Described above are example embodiments. It is, of course, not possible to describe every conceivable combination of components or methodologies, but one of ordinary skill in the art will recognize that many further combinations and permutations of the example embodiments are possible. Accordingly, this application is intended to embrace all such alterations, modifications and variations that fall within the spirit and scope of the appended claims interpreted in accordance with the breadth to which they are fairly, legally and equitably entitled.

The invention claimed is:

1. An apparatus, comprising:
a first display having a first size and a first orientation;
a second display having a second size that is less than the first size and a second orientation that is different from the first orientation; and
a scanner co-located with the second display;
display logic coupled with the first display and the second display;
one of a group consisting of a cash dispenser and a cash recycler;
a user interface device selected from a group consisting of a card reader and a wireless reader;
automatic transaction machine logic coupled with the display logic, the scanner, the one of the group consisting of the cash dispenser and cash recycler, and the user interface device, wherein the automatic transaction machine logic is operable to employ the display logic, the scanner, the one of the group consisting of the cash dispenser and cash recycler, and the user interface device to perform a financial transaction;
the display logic is operable to allow a user to select a mode of operation for the first display and the second display;
wherein the mode of operation is selected from a group consisting of displaying transaction information on the first display while blanking the second display, displaying transaction information on the second display while blanking the first display, displaying transactional data on the first display and displaying public data on the second display.

2. The apparatus set forth in claim 1, the display logic is operable to toggle between a first mode of operation selected from the group consisting of displaying transaction information on the first display while blanking the second display, displaying transaction information on the second display while blanking the first display, displaying transactional data on the first display and displaying public data on the second display and a second mode of operation selected from the group consisting of displaying transaction information on the first display while blanking the second display, displaying transaction information on the second display while blanking the first display, displaying transactional data on the first display and displaying public data on the second displaying.

3. The apparatus set forth in claim 1, wherein the display logic is operable to save a user selection as a default mode for the user.

4. The apparatus set forth in claim 1, further comprising one of a group consisting of a service teller call button, service teller call light, a touch screen interface coupled with the first display, a touch screen interface coupled with the second display, one or more consumer facing cameras, one or more microphones, one or more speakers, an encrypting Personal Identification Number pad, a headphone jack, a receipt printer, an Europay, MasterCard, and Visa card reader that is configured for one of a group consisting of short-edge and long-edge card insertion, a DIP card reader, a 2D barcode scanner, document scanner, signature scanner, Quick Response code scanner, a mixed deposit module opening for receipt of currency and documents, and a biometric reading device.

5. The apparatus set forth in claim 4, wherein the first display is orientated generally vertically and the second display is orientated generally horizontally.

6. The apparatus set forth in claim 5, wherein the first display is at a first height and the second display is at a second height that is lower than the first height.

7. The apparatus set forth in claim 6, wherein the second height is low enough to allow a user in a wheelchair to interact with the second display.

8. The apparatus set forth in claim 1, further comprising a second scanner co-located with the first display.

9. An apparatus, comprising:
a first display having a first size and a first orientation;
a second display having a second size that is less than the first size and a second orientation that is different from the first orientation; and
a scanner co-located with the first display;
display logic coupled with the first display and the second display;
one of a group consisting of a cash dispenser and a cash recycler;
a user interface device selected from a group consisting of a card reader and a wireless reader;
automatic transaction machine logic coupled with the display logic, the scanner, the one of the group consisting of the cash dispenser and cash recycler, and the user interface device, wherein the automatic transaction machine logic is operable to employ the display logic, the scanner, the one of the group consisting of the cash dispenser and cash recycler, and the user interface device to perform a financial transaction;

the display logic is operable to allow a user to select a mode of operation for the first display and the second display;

wherein the mode of operation is selected from a group consisting of displaying transaction information on the first display while blanking the second display, displaying transaction information on the second display while blanking the first display, displaying transactional data on the first display and displaying public data on the second display.

10. The apparatus set forth in claim 9, the display logic is operable to toggle between a first mode of operation selected from the group consisting of displaying transaction information on the first display while blanking the second display, displaying transaction information on the second display while blanking the first display, displaying transactional data on the first display and displaying public data on the second display and a second mode of operation selected from the group consisting of displaying transaction information on the first display while blanking the second display, displaying transaction information on the second display while blanking the first display, displaying transactional data on the first display and displaying public data on the second displaying.

11. The apparatus set forth in claim 9, wherein the display logic is operable to save a user selection as a default mode for the user.

12. The apparatus set forth in claim 9, further comprising one of a group consisting of a service teller call button, service teller call light, a touch screen interface coupled with the first display, a touch screen interface coupled with the second display, one or more consumer facing cameras, one or more microphones, one or more speakers, an encrypting Personal Identification Number pad, a headphone jack, a receipt printer, an Europay, MasterCard, and Visa card reader that is configured for one of a group consisting of short-edge and long-edge card insertion, a DIP card reader, a 2D barcode scanner, document scanner, signature scanner, Quick Response code scanner, a mixed deposit module opening for receipt of currency and documents, and a biometric reading device.

13. The apparatus set forth in claim 12, wherein the first display is orientated generally vertically and the second display is orientated generally horizontally.

14. The apparatus set forth in claim 13, wherein the first display is at a first height and the second display is at a second height that is lower than the first height.

15. The apparatus set forth in claim 14, wherein the second height is low enough to allow a user in a wheelchair to interact with the second display.

* * * * *